United States Patent
Crosby et al.

(10) Patent No.: US 9,463,332 B2
(45) Date of Patent: Oct. 11, 2016

(54) PERSONAL TUNER WITH BIOSENSOR AND BIOSCANNER

(71) Applicant: CAMS Medical Instruments, Inc., Orlando, FL (US)

(72) Inventors: Charles J. Crosby, Orlando, FL (US); Nelson Conrad Dove, Hazel Green, AL (US)

(73) Assignee: CAMS Medical Instruments, Inc., Orlando, FL (US)

( * ) Notice: Subject to any disclaimer, the term of this patent is extended or adjusted under 35 U.S.C. 154(b) by 648 days.

(21) Appl. No.: 13/952,091

(22) Filed: Jul. 26, 2013

(65) Prior Publication Data

US 2013/0310905 A1 Nov. 21, 2013

Related U.S. Application Data

(63) Continuation-in-part of application No. 11/859,413, filed on Sep. 21, 2007, now abandoned, and a continuation-in-part of application No. 11/441,483, filed on May 26, 2006, now Pat. No. 7,883,534, and a continuation-in-part of application No. 10/084,008, filed on Feb. 27, 2002, now Pat. No. 7,077,857.

(Continued)

(51) Int. Cl.
*A61N 5/06* (2006.01)
*A61N 7/00* (2006.01)
(Continued)

(52) U.S. Cl.
CPC ............... *A61N 5/06* (2013.01); *A61H 23/02* (2013.01); *A61N 7/00* (2013.01); *A61B 2017/00128* (2013.01); *A61H 23/0245* (2013.01); *A61N 2007/006* (2013.01)

(58) Field of Classification Search
CPC .... A61H 1/00; A61H 23/02; A61H 23/0218; A61H 23/0236; A61H 23/0245; A61H 2023/0209; A61H 2023/0227; A61N 1/16; A61N 5/06; A61N 5/0613; A61N 2005/0631; A61N 2005/0652; A61N 2005/0644; A61N 7/00; A61N 2007/006; A61B 2017/00128
See application file for complete search history.

(56) References Cited

U.S. PATENT DOCUMENTS

| | | | |
|---|---|---|---|
| 1,510,080 | A | 9/1924 | Murphy |
| 2,213,031 | A | 8/1940 | Wolfskill |
| 2,306,909 | A | 12/1942 | Sykes |
| 3,371,234 | A | 2/1968 | Cady |

(Continued)

OTHER PUBLICATIONS

Raphaell, Katrina, "Lemurian Seed Crystals", 1994, Royal Priest Research, The Crystal Buzz International Newsletter, Issue 12.*

(Continued)

*Primary Examiner* — Valerie L Woodward
(74) *Attorney, Agent, or Firm* — Brian S. Steinberger; Law Offices of Brian S. Steinberger, P.A.

(57) ABSTRACT

Portable therapeutic treatment devices and methods with a triangular arrangement of crystals in an induction coil with an external wrapped coil for sensing effected area body part emissions. A biosensor/bioscanner sensor can be used as an indicator to find an effected body part needing treatment and determine when treatment has been effective. The device can be passed over a body until a RED LED light indicates an effected part needing treatment. Treatment can occur with approximately 8 Hz emissions, and the sensor will indicate when the effected area has reached a treated state of approximately 8 Hz by lighting a GREEN LED light. Treatment can occur within approximately 2 minutes. A variety of ailments can be treated such as but not limited to inflammations, nerve problems, joint-pain, muscle-pain, gall bladder problems, and the like.

17 Claims, 12 Drawing Sheets

Related U.S. Application Data

(60) Provisional application No. 60/950,723, filed on Jul. 19, 2007, provisional application No. 60/685,448, filed on May 27, 2005.

(51) Int. Cl.
  *A61H 23/02* (2006.01)
  *A61B 17/00* (2006.01)

(56) References Cited

U.S. PATENT DOCUMENTS

| | | | | |
|---|---|---|---|---|
| 4,221,986 A | * | 9/1980 | Besson | H03H 9/177 310/344 |
| 4,708,127 A | * | 11/1987 | Abdelghani | A61H 23/0245 310/319 |
| 4,869,666 A | | 9/1989 | Talass | |
| 5,086,788 A | * | 2/1992 | Castel | A61H 23/0245 601/21 |
| 5,158,070 A | | 10/1992 | Dory | |
| 5,230,334 A | | 7/1993 | Klopotek | |
| 5,562,597 A | * | 10/1996 | Van Dick | A61N 1/16 600/14 |
| 5,591,219 A | * | 1/1997 | Dungan | A61N 5/06 250/504 H |
| 5,989,202 A | | 11/1999 | Noda | |
| 6,048,301 A | * | 4/2000 | Sabuda | A61N 5/06 600/1 |
| 6,113,559 A | | 9/2000 | Klopotek | |
| 6,200,331 B1 | * | 3/2001 | Swartz | A61N 1/08 607/1 |
| 6,217,530 B1 | | 4/2001 | Martin | |
| 6,238,421 B1 | | 5/2001 | Gunther | |
| 6,500,198 B1 | * | 12/2002 | Southard | A61N 5/0616 607/2 |
| 7,410,769 B2 | * | 8/2008 | Burroughs-Tencza | C12Q 1/04 435/235.1 |
| 7,883,534 B1 | | 2/2011 | Crosby | |
| 8,443,811 B1 | | 5/2013 | Crosby | |
| 8,534,292 B1 | | 9/2013 | Crosby | |
| 9,233,261 B1 | | 1/2016 | Crosby | |
| 2003/0181949 A1 | * | 9/2003 | Whale | A61N 5/0613 607/2 |
| 2004/0002744 A1 | * | 1/2004 | Dungan | A61N 5/0618 607/88 |

OTHER PUBLICATIONS

Liss Body Stimulator (Zero d.c.), Professional Instrument Manual, SBL 502-B, 1997, 5 pages.
Crosby, Tensam Professional Manual, 2001, 8 pages.
Oschman, Energy Medicine, The Scientific Basis, Churchill Livingstone Publishers, 2000, pp. 51, 61 and 184.
Hund, Uses and Possibilities of Piezoelectric Oscillators, Proceedings of the Institute of Radio Engineers, 1926, pp. 47-469, vol. 14.

* cited by examiner

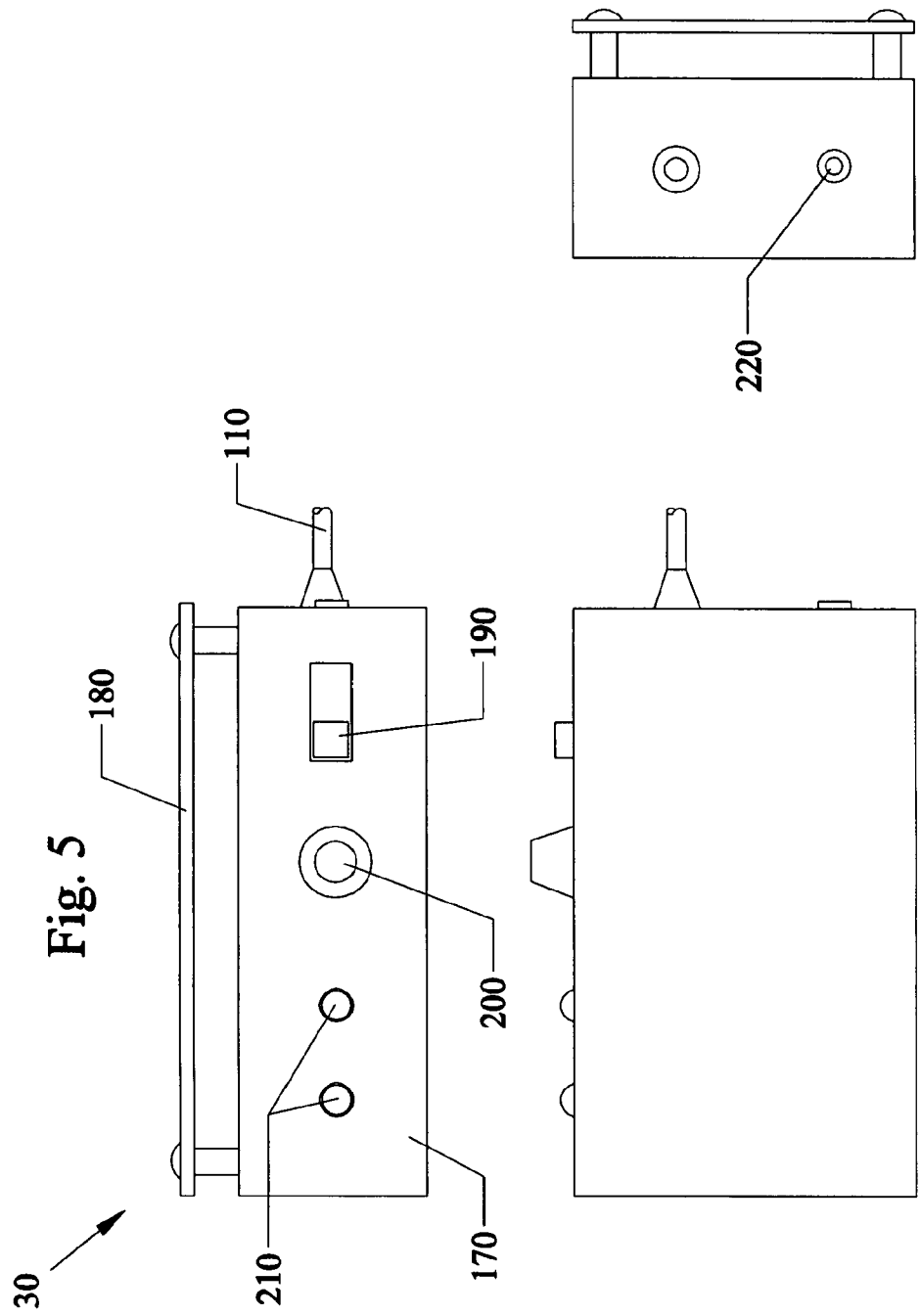

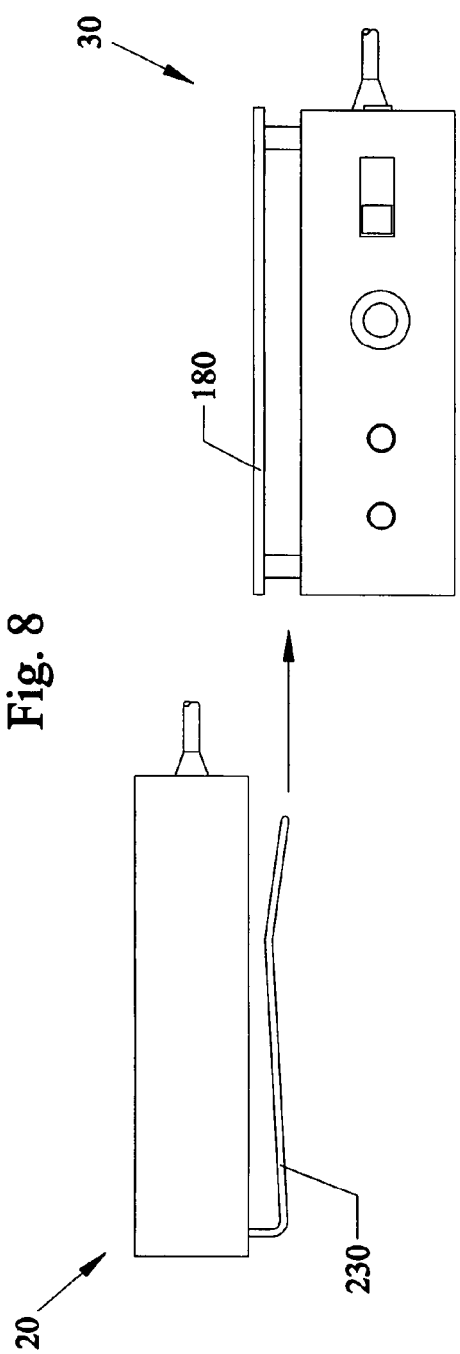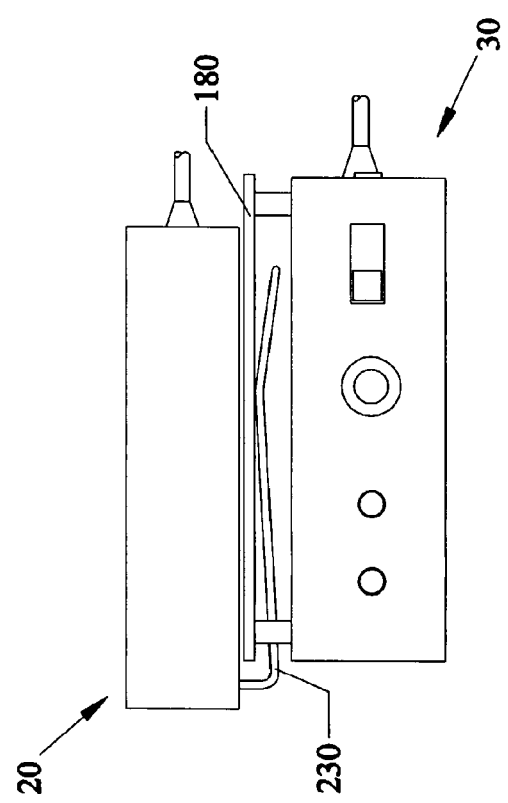

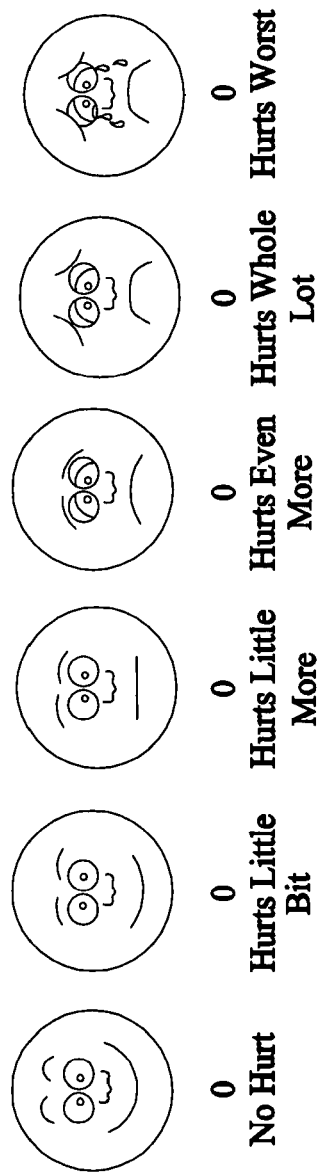

PERSONAL TUNER WITH BIOSENSOR AND BIOSCANNER

This invention is a Continuation-In-Part of U.S. patent application Ser. No. 11/859,413 filed Sep. 21, 2007, now abandoned, which claims the benefit of priority to U.S. Provisional Patent Application 60/950,723 filed Jul. 19, 2007, and is a Continuation-In-Part of U.S. patent application Ser. No. 11/441,483 filed May 26, 2006, now U.S. Pat. No. 7,883,534, which claims the benefit of priority to U.S. Provisional Patent Application Ser. No. 60/685,448 filed May 27, 2005, and is a Continuation-In-Part of U.S. patent application Ser. No. 10/084,008 filed Feb. 27, 2002, now U.S. Pat. No. 7,077,857. The entire disclosure of each of the applications listed in this paragraph are incorporated herein by specific reference thereto.

FIELD OF INVENTION

This invention relates to medical therapy treatment devices, and in particular to devices, apparatus and methods of using portable single handheld tools that generate vibratory emissions, ultrasonic emissions, light pulses and/or electromagnetic emissions which focus the energy emissions to patients for therapeutic treatments which provides operational feedback to both the practitioner and the patient.

BACKGROUND AND PRIOR ART

Ultrasound and vibratory type emitters have been used for medical therapeutic applications over the years. Various therapeutic devices have applied ultrasonic oscillations and vibrations to affected body parts to relax muscles, quicken blood flow circulation, enhance healing of the skin, etc. See For example, U.S. Pat. No. 4,708,127 to Abdelghami; U.S. Pat. Nos. 5,230,334 and 6,113,559 to Klopotek; and U.S. Pat. No. 5,989,202 to Noda et al.

However, these devices and systems have practical type limitations. For example, most of these devices are limited to direct contact of a portion of the device itself against the skin of the patient. As a result, the field of application is generally restricted to the areas directly beneath the skin contact point. The body contacting requirement does not allow these devices to easy slide over and across one's skin to different areas to be treated. Thus, moving these devices to other body areas usually requires that the device be physically raised, moved and lowered again to the area to be treated.

Furthermore, these devices are generally limited to using acoustical type vibratory signal emissions from a single generator type unit such as an electromagnetic generator, and does not use other energy sources, nor applies other energy emissions for treatments.

Still furthermore, the single generators are generally limited to generating only fixed frequency outputs.

The subject inventor has previously sold a basic handheld tool entitled: Tens Cam having a single fixed frequency generating crystal that solely relied on an electromagnetic induction coil to drive a single crystal. The Tens Cam unit consisted only of a Coil wrapped around a longitudinal Crystal, powered by LISS BODY STIMULATOR power pack, where LEDs (light emitting diodes) are used to indicate power being turned on.

The operation of the Tens Cam used a fixed frequency of approximately 8 Hertz that was generated by an electromagnetic source in a narrow beam having a diameter of approximately 1 to approximately 2 millimeters. The delay time for therapeutic effects of the Tens Cam unit was between approximately two to approximately four (4) minutes.

The Tens Cam unit had problems due to its' weight of approximately one pound and rough appearance and oblong shape. Taking up to four minutes to generate therapeutic effects on the patient was difficult to do over continuous treatments, since it required the operator to physically hold the one pound unit in a raised position above the patient being treated. Thus, operator fatigue was an inherent result of using this unit.

By physically holding the vibrating unit above a patient throughout a several minute treatment process the operator received direct vibratory effects from the unit. The combination of constantly holding the weight of the unit and the direct vibratory effects, along with the operator being constantly within the generation field of the unit created side effects such as but not limited to fatigue and malaise for the operator. Operators repeatedly using the Tens Cam have complained of side effects of medium nerve paraethias, which is a numbness and tingling effect to their hands and fingers.

Additional problems with the Tens Cam unit as with other electromagnetic and with vibratory units is that all these units can be known to give off heat which has caused tissue damage. Furthermore, theses prior art type units have limitations as to the tissue penetration being achieved, since the tissue penetration depth is limited by the mechanical nature of the vibrations.

All of the prior art units are limited to generating energy directly from electric power supplies and fail to take in additional energy to aid in the therapy treatment. Ambient energy is not used, saved or overcome by the prior art devices.

Prior art units have been known to cause injuries directly to the patients. Using a strictly handheld supported vibrating and/or heat generating and/or electrically driven device can potentially injure the patients themselves or the operator, if the operator directly contacts the patients with the devices. Electric shocks, burns and other damage can be caused by the patients coming into direct contact with many prior art therapy devices.

The prior art devices are directed toward transmitting signals toward the patient. None of the prior covers devices, systems and methods cover actively, and in real-time sensing the outcome of the therapy treatments. The prior art does not allow for the treatment/therapy operator to monitor the physical conditions and/or status of the patient during a therapy treatment/session.

Thus, the need exists for solutions to the problems with the prior art devices.

SUMMARY OF THE INVENTION

A primary objective of the invention is to provide handheld tools, apparatus, device and method for therapy treatments that does not have to be in direct contact with the skin surface of a patient, that does not have the tissue depth penetration limitations of electromagnetic sources and vibratory devices, and which provides operational feedback of a physical condition and/or status to both the practitioner and the patient.

A secondary objective of the invention is to provide a handheld tool, apparatus, device and method for therapy treatments that can combine an energy generating source along with an ambient receiver to sense and provide readings of medical treatment effects at resonating emissions of approximately 7 to approximately 8 Hertz, and which provides operational feedback of a physical condition and/or status to both the practitioner and the patient.

A third objective of the invention to provide a handheld tool, apparatus, device and method for therapy treatments that can alternate between a fixed frequency output and a variable frequency range of emissions to include the resonant frequency of the patient being treated of between approximately 4 to approximately 15 Hertz, and which provides operational feedback of a physical condition and/or status to both the practitioner and the patient.

A fourth objective of the invention is to provide a handheld tool, apparatus, device and method for therapy treatments that can be positioned toward a body part to be treated, and which provides operational feedback of a physical condition and/or status to both the practitioner and the patient.

A fifth objective of the invention is to provide a handheld tool, apparatus, device and method for therapy treatments that reduces and eliminates patient injury risks, and allows for most any body tissue to be easily reached and treated by the tool, and which provides operational feedback of a physical condition and/or status to both the practitioner and the patient.

A sixth objective of the invention is to provide a handheld tool, apparatus, device and method for therapy treatments that reduces and potentially eliminates fatigue and malaise injuries to the tool operator of previously known devices, and which provides operational feedback of a physical condition and/or status to both the practitioner and the patient.

A seventh objective of the invention is to provide a handheld tool, apparatus, device and method for therapy treatments that can achieve therapeutic results within approximately 2 (two) minutes as compared up to 4 (four) minutes that was required with previous tools, and which provides operational feedback of a physical condition and/or status to both the practitioner and the patient.

An eighth objective of the invention is to provide a sensitive yet very compact and affordable tool, apparatus, device and method for therapy treatments which also provides operational feedback of a physical condition and/or status to both the practitioner and the patient on an ongoing basis.

Various embodiments for using the invention are disclosed. One embodiment uses a handheld tool having biosensor/bioscanning feedback that allows the practitioner to easily move the tool about the patient. Another embodiment has the novel biosensor/bioscanner tool mounted on a boom stand that can be positioned adjacent to the patient being treated.

Portable vibratory therapeutic treatment invention, devices, and methods that can house a triangular arrangement of small longitudinal crystals wrapped in an induction coil and also have an external wrapped coil for sensing effected area body part emissions. The device can generate a fixed output of approximately 7 to approximately 8 Hertz while the housing is positioned up to approximately 18 inches over the body part being treated with a light beam aimed at the area to be treated. A biosensor/bioscanner sensor can be used as an indicator to both find an effected body part that needs to be treated and is used to determine when the effected body part has been effectively treated. The sensor can include a torroidal coil wrapped about a ferrous coil placed over the housing that can sense emissions from an area that needs treatment.

Users can pass the unit over a body until a RED LED light on the sensor stays lighted when the device has reached an effected body part area needing treatment. The device can then treat the area needing treatment with the approximately 8 Hz emissions, and the sensor will then indicate when the effected area has reached a treated state of approximately 8 Hz by lighting up a GREEN LED light. Treatment effectiveness can occur within approximately 2 minutes of being treated. The invention can be used for treating a variety of ailments such as inflammations, nerve problems, joint pain, muscle pain, as well as gall bladder type problems.

Further objects and advantages of this invention will be apparent from the following detailed description of a presently preferred embodiment which is illustrated schematically in the accompanying drawings.

BRIEF DESCRIPTION OF THE FIGURES

FIG. 5 is a front view of the amplifier of the preceding figures.

FIG. 6 is a top view of the amplifier of FIG. 5.

FIG. 7 is an end view of the amplifier of FIG. 5.

FIG. 8 is a side view of the cam unit and amplifier ready to be mounted to one another.

FIG. 9 is another view of the cam unit and amplifier mounted with one another.

FIG. 13 shows a visual analogy scale (VAS) that was used with testing of the invention.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The invention is a Continuation-In-Part of U.S. patent application Ser. No. 11/441,483 filed May 26, 2006, now U.S. Pat. No. 7,883,534, which is a Continuation-In-Part of U.S. patent application Ser. No. 10/084,008 filed Feb. 27, 2002, now U.S. Pat. No. 7,077,857, and this invention claims the benefit of priority to U.S. provisional patent application Ser. No. 60/685,448 filed May 27, 2005, all of which are incorporated by reference.

The referenced numbers of the figures will now be described.

10) Transmitter device.
20) Tens unit
30) Amp unit.

Figure 1:
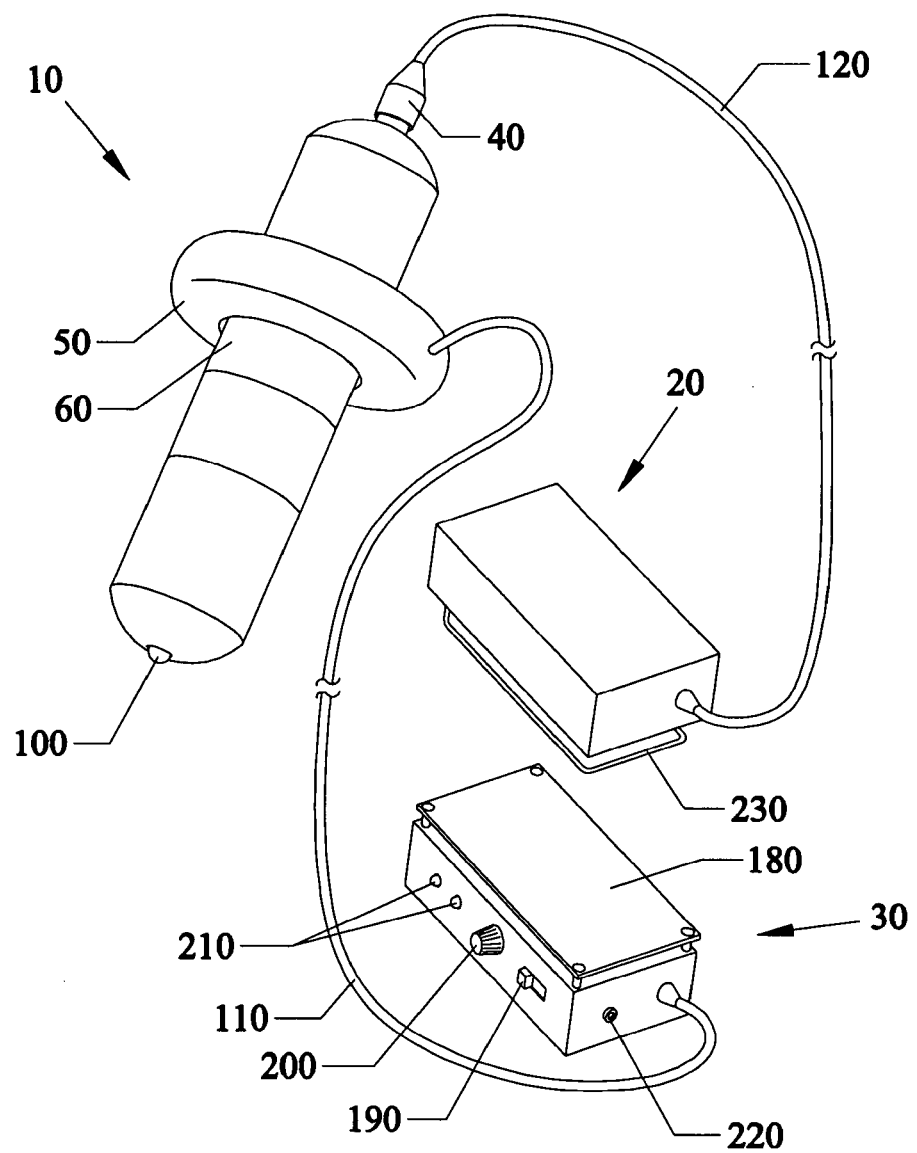
FIG. 1 is a perspective view of the novel biosensor/bioscanner medical treatment device with cam unit and amplifier.
Figure 2:
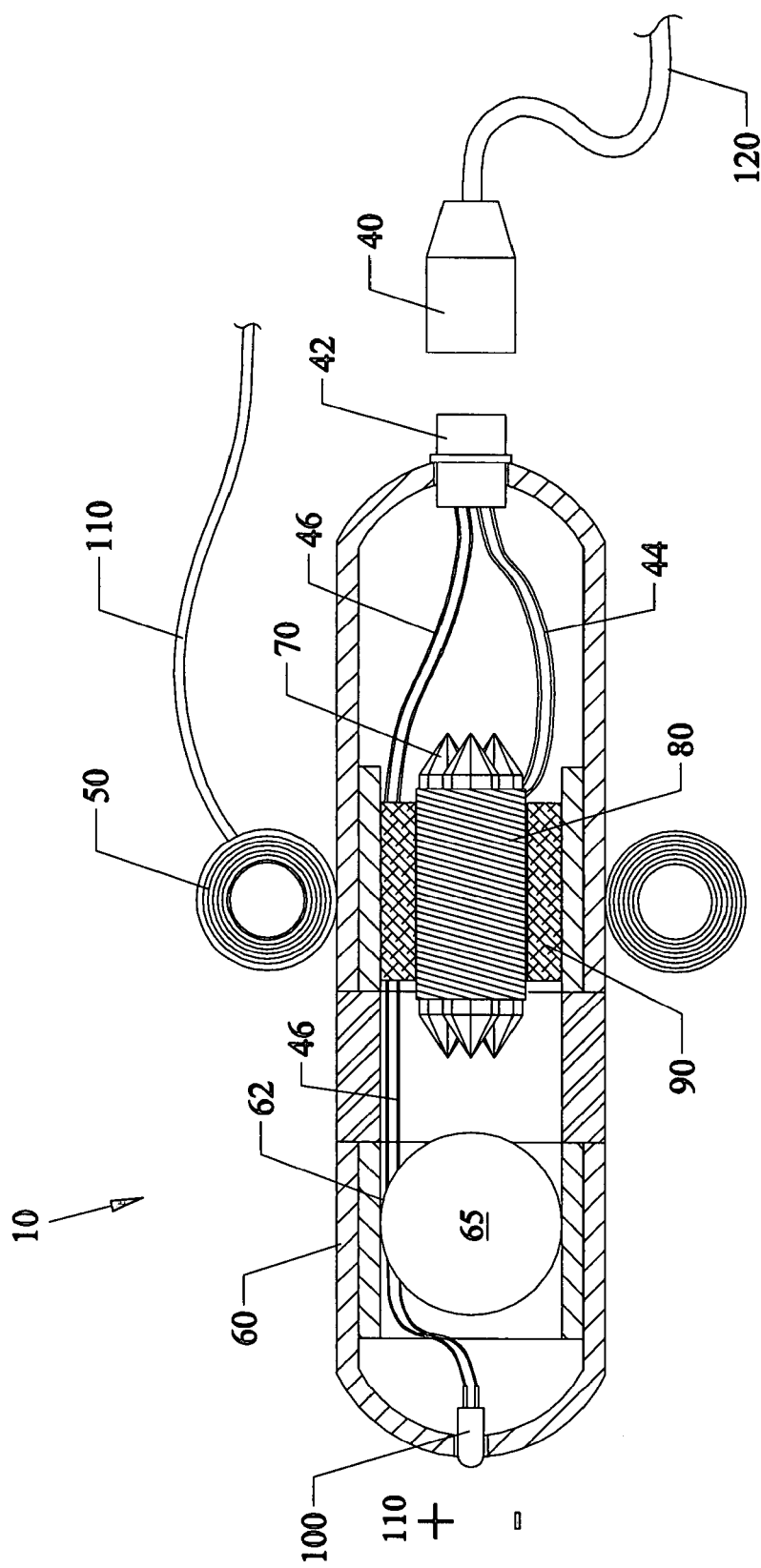
FIG. 2 is a cross-sectional view of the novel treatment device of FIG. 1.

40) Female Connector.
42) Male Connector
44) conductor
46) conductor
50) External coil.
60) Transmitter case.
62) internal pressure fit
65) sphere lens
70) Crystals.
80) Internal coil.
90) Crystal packing.
100) Indicator LED.
110) Cable from coil to amplifier.
120) Cable from tens unit to transmitter.
130) Transmitter mounted to floor stand.
140) Patient.
150) Hand held transmitter.
160) Technician.
170) Amplifier housing.
180) Clip plate attached to amplifier for mounting of tens unit.
190) On/Off switch.
200) Potentiometer.
210) Red & green LED's.
220) Charging plug receptacle.
230) Tens unit clip for attachment to amplifier.
300) stand
302) boom arm
304) pivoting joint
306) stand leg FIG. 1 is a perspective view of the novel biosensor/bioscanner medical treatment device 10 with cam unit 20 and amplifier 30. FIG. 2 is a cross-sectional view of the novel treatment device 10 of FIG. 1. Referring to FIGS. 1-2, the transmitter device 10 can include a generally cylindrical sleeve housing 60 that can be formed from PVC material, having a rounded front end with an indicator LED (light emitting diode) 100, and rounded rear end with a male connector end 42 extending therefrom. Inside the front end of the housing 60 can be an optional sphere lens 65, formed from silicon dioxide, quartz, and the like, within a press joint 62, similar to that described in reference to parent patent application Ser. No. 10/084,008 filed Feb. 27, 2002, now U.S. Pat. No. 7,077,857, which is incorporated by reference.

Inside a mid-part of the housing 60 can be three (3) elongated multi-faceted crystals 70, such as lemurian crystals, preferably arranged in a triangular configuration. Each of the elongated crystals can have dimensions of approximately 1 inch long and approximately ¼ inch in diameter. Although three (3) crystals are shown and described, it is possible for the invention to work with more crystals, such as four or more.

The triangular arrangement of crystals 70 can be wrapped in a bifilar coil 80, which functions as an inner coil to cancel out the magnetic component. The inner coil can include up to approximately 400 winding turns. The wrapped crystals 70 within the inner coil 80 can be supported within the housing 60 by an insulative cushion sleeve 90 such as wrapped electrical tape, foam, combinations thereof, and the like.

Surrounding the housing 60 can be an external coil 50, such as a torroidal coil, which is used to pick up the sensed variance from the three crystals 70, when the crystals are used in a sensing mode, which will be described below.

The modulation of the local scalar field caused by the ailment being treated is detected by moving the toroidal coil through the modulated field. The crystals which are placed inside the toroid seem to act as amplifiers of the scalar field modulation. The output of the toroidal coil is applied to low noise, high gain amplifiers which in turn send the amplified signal to the high and low pass filters. The outputs of the filters are used to turn on the appropriate LED indicators.

Referring to FIGS. 1-2, the device 10 can be attached by cable 120 that is attached to tens unit 20, which is described in detail in parent patent application 10/084,008 filed Feb. 27, 2002, now U.S. Pat. No. 7,077,857, which is incorporated by reference. Cams unit 120 can be connected by a cable 120 to a female connector 40 that can be mateably attached to male connector 42 and internal conductors 44 connected to internal coil 90 and conductors 46 that connects to LED indicator 100.

Underneath the tens unit 20 can be a clip 230, which will be described in reference to FIGS. 8-9. The external torroidal coil 50 about housing 60 can be connected to the amplifier unit 30 by a cable 110. The amplifier unit 30 can have a charging plug receptacle 220 that allows for an internal battery to be recharged over time, an on/off switch 190, such as a toggle switch, a potentiometer 200 and a pair of spaced apart LEDs 210(one of which can be green, and the other can be red).

Figure 3:
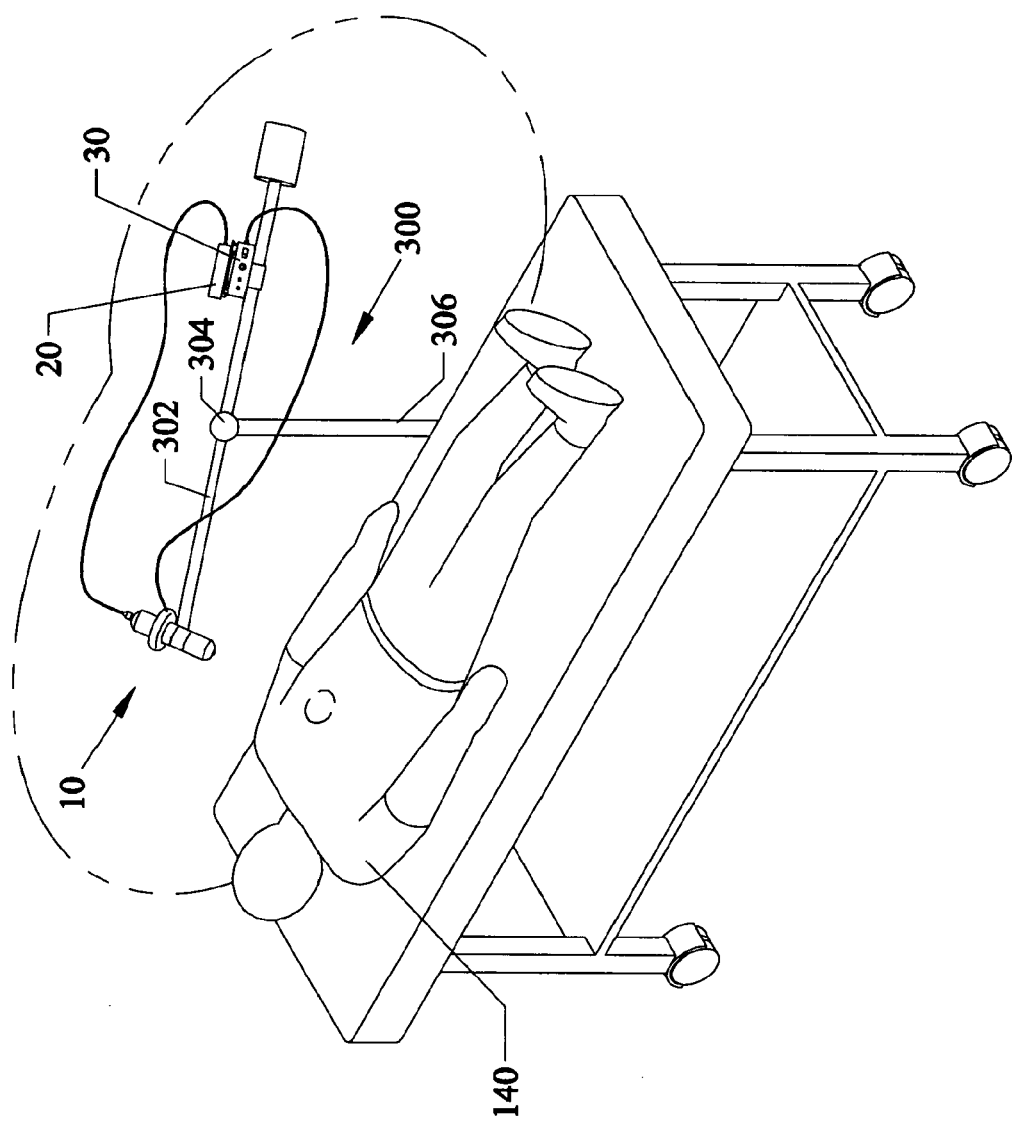
FIG. 3 is a perspective view of the treatment device with cam unit and amplifier of FIG. 1 mounted on a stand being used with a patient.

FIG. 3 is a perspective view of the treatment device 10 with cam unit 20 and amplifier 30 of FIG. 1 mounted on a the boom arm 302 of a stand 300, where the arm 302 is attached to a vertical leg 306 by an adjustable pivoting joint 304, which allows for the arm 302 to raise and lower and rotate relative to the support leg(s) 306.

Figure 4:
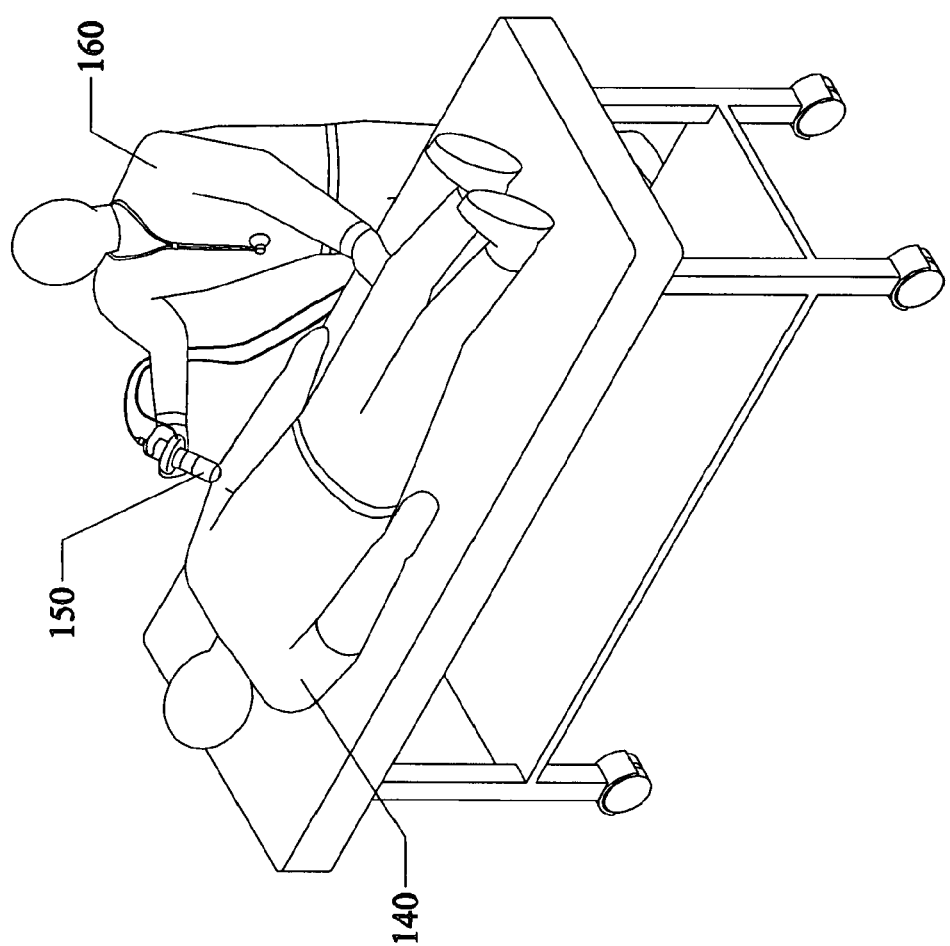
FIG. 4 is a perspective view of the treatment device with cam unit and amplifier of FIG. 1 being used by a medical practitioner.

FIG. 4 is a perspective view of a handheld version 150 of the treatment device 10 previously described, connected to unseen tens unit 20 and unseen amplifier unit 30 of FIG. 1 being used by a medical practitioner 160, such as a medical technician, and the like, for treating a patient 140 that can be in a laid down position.

FIG. 5 is a front view of the amplifier 30 of the preceding figures, which shows the LEDS 210, potentiometer 200, on/off switch 190, and connecting cable 110 that connects to the external coil 50 on the device housing 60 of the preceding figures. FIG. 6 is a top view of the amplifier 30 of FIG. 5. FIG. 7 is an end view of the amplifier 30 of FIG. 5 showing the charging plug receptacle 220.

FIG. 8 is a side view the tens cam unit 20 with clip attachment 230 and amplifier 30 with pre-attached clip plate 180 ready to be mounted to one another.

FIG. 9 is another view of the cam unit and amplifier mounted with one another after the clip 230 of the tens cam unit 20 slips through and between the pre-attached clip plate 180 and amplifier 30.

Figure 10:
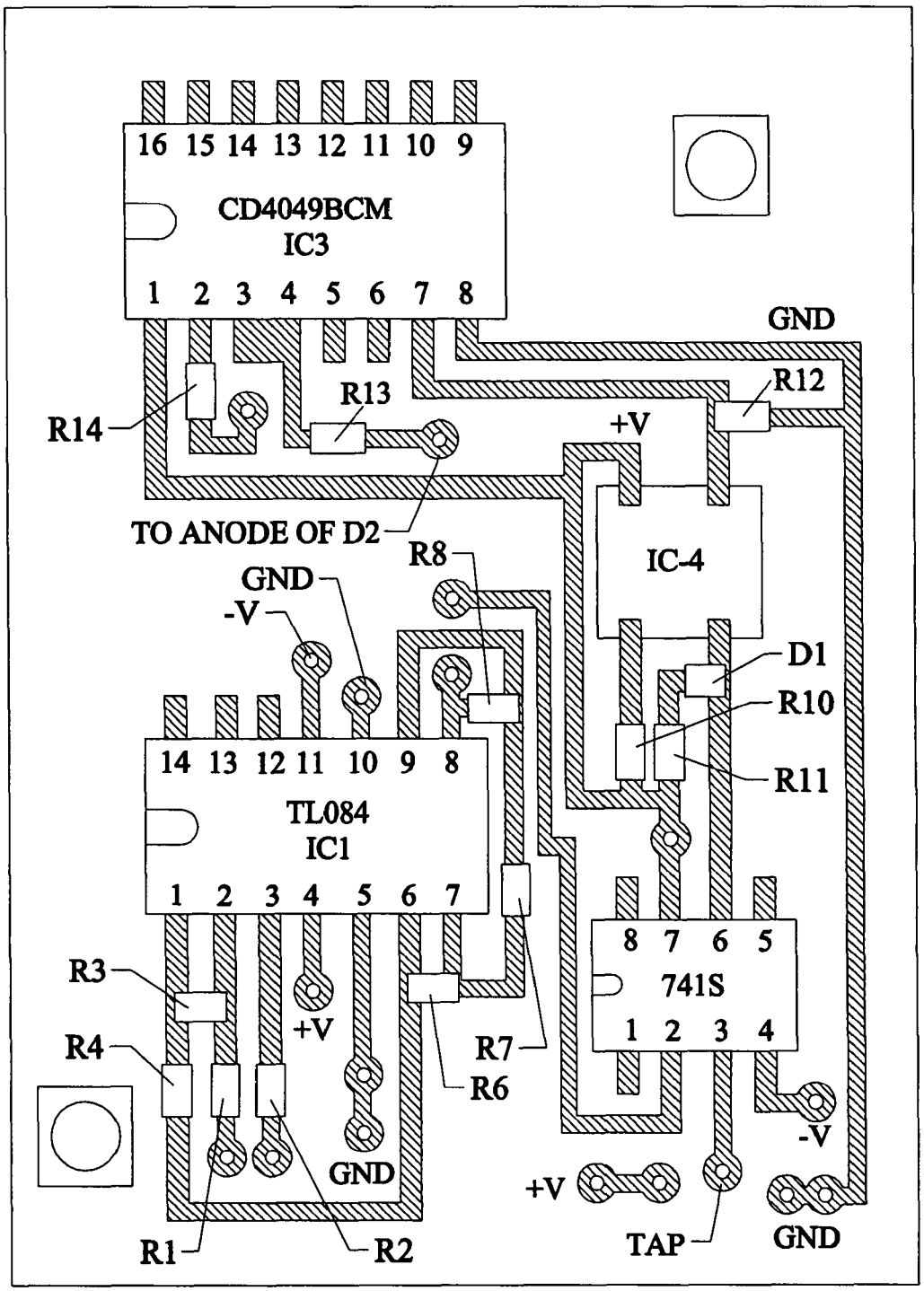
FIG. 10 shows the printed circuit board.
Figure 11A:
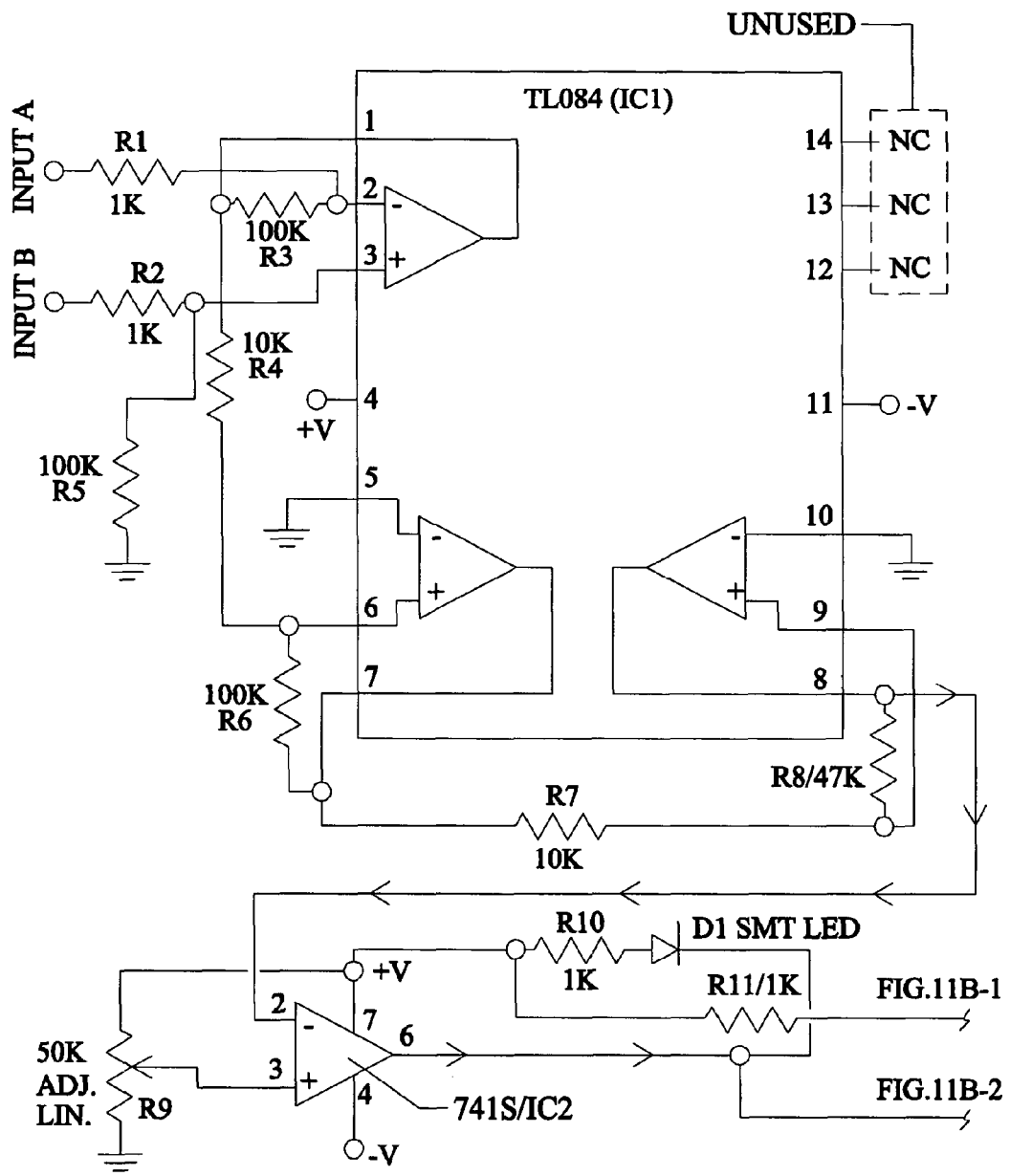
FIGS. 11A and 11B show a schematic of the printed circuit board.
Figure 11B:
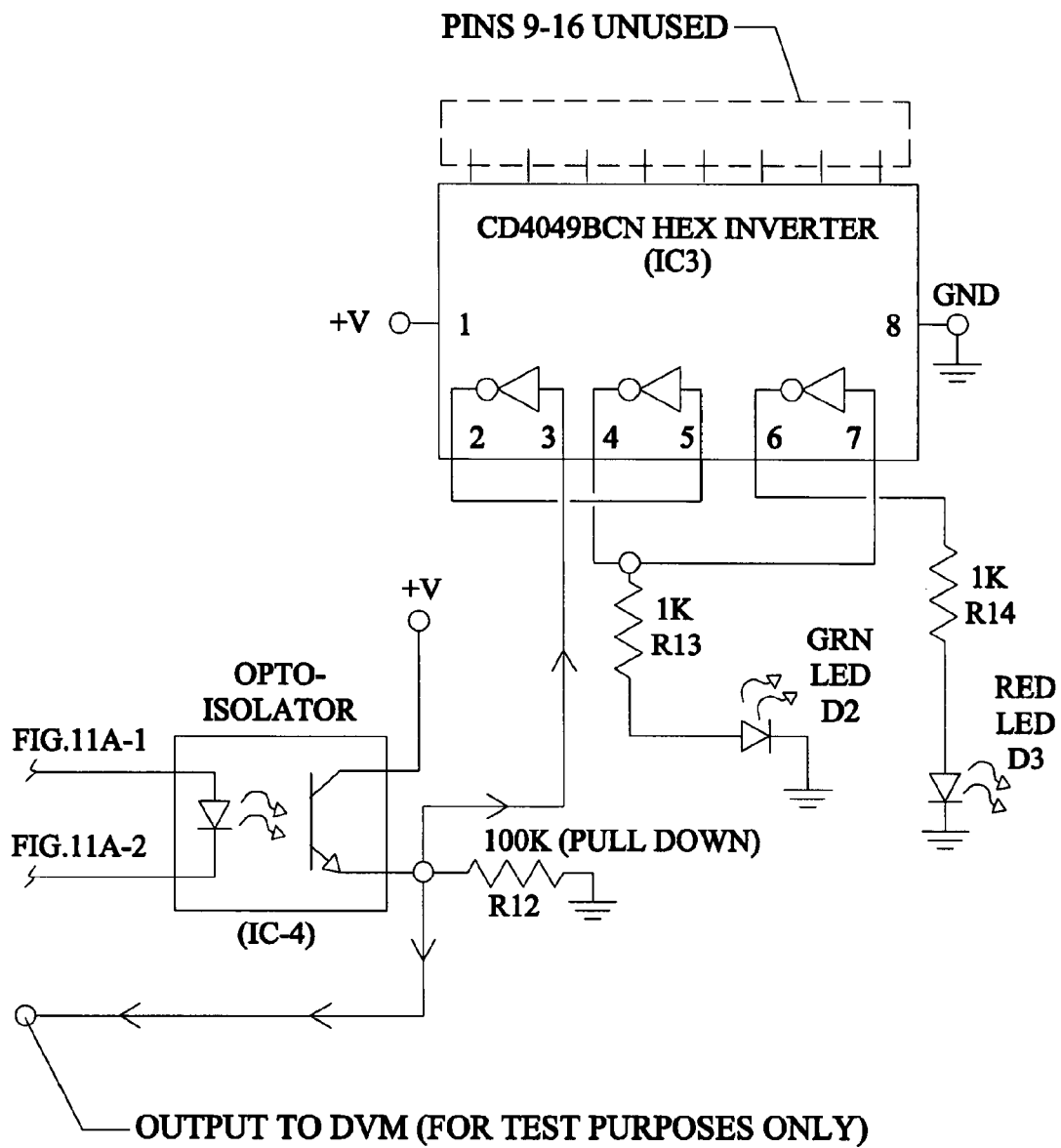

FIG. 10 shows the printed circuit board that can be used with the invention. FIGS. 11A and 11B show a schematic of the printed circuit board. FIG. 12 is another schematic of the printed circuit board.

In operation, the Tens Cam unit 20, can be similar to the one described in parent patent application Ser. No. 10/084,008 filed Feb. 27, 2002, now U.S. Pat. No. 7,077,857, which is incorporated by reference. The tens cam unit 20 can allow for an approximately 15,000 Hertz square wave carrier which can be rectified, varying from zero to a maximum of approximately 4 milli amperes. A first modulating signal of approximately 15 Hertz can provide an "on" time of approximately 50 milliseconds and an "off" time of approximately 16.7 milliseconds.

A second modulating signal of approximately 500 Hertz changes the "on" time series of approximately 15,000 Hertz carrier pulses (approximately 750 pulses in approximately 50 milliseconds) into approximately 25 smaller bursts of approximately 15 pulses each of the 15,000 Hertz carrier signal (approximately 375 pulses in the same 50 milliseconds). The signals pass through the triangular arrangement of elongated Lemurian crystals 70 by the electromagnetic coils 80 wrapped about crystal 70. An on/off switch on the tens cam unit 20 can provide power to the internal coils 80 so that, a fixed emission of approximately 7.75 Hertz (approximately 8 Hertz) can be emitted from tool 10.

Signals passing from the front end of the triangular arranged crystals 70 are further amplified and diffused by lens 65 and pass into the air in a beam 110 having a diameter of approximately 5 to approximately 6 cm. The tool 10 can emit a fixed output emission of approximately 8 Hertz.

Co-inventor, Dr. Charles Crosby, MD has detailed in parent patent application Ser. No. 10/084,008 filed Feb. 27, 2002, now U.S. Pat. No. 7,077,857, which is incorporated by reference, that treatises have detailed how the solid state biochemistry and the piezoelectric characteristics of the cell wall relates to the electrical properties of the living cellular matrix. See for example, the book entitled: Energy Medicine, The Scientific Basis by Dr. James L. Oschman, Churchill Livingstone Publishers, 2000, on pages 51, 61 and 184. This book references the works of Dr. Robert Becker, MD, and his contribution of the perineural control system as it relates to limb growth and regeneration. Here the Schmann Resonance Theory is that the average alpha brain wave frequency in humans is 7.86 Hz, and that human tissue resonates at 7.86 Hz. The subject inventor has incorporated these treatise teachings along with his tested inventions in Osteopathy Chiropractic treatments where the combination of structural and electromagnetic integration allows for the release of toxins and health improvements.

In operation, a health practitioner can position the novel invention tool 10 to a selected position over the patient 140 up to approximately 18 inches over a particular body part being treated. The effected body part can be a gall bladder, joint pain, back pain, tissue damage, bone ligaments, organs, and the like. Additionally, the novel tool 1 can have therapeutic treatments for patients suffering from chronic type pain, joint pains, back pains, neck pains, hip pains, and shoulder pains.

As described in parent patent application Ser. No. 10/084,008 filed Feb. 27, 2002, now U.S. Pat. No. 7,077,857, which is incorporated by reference, the testing of the novel tool 10 using the three operational modes previously described has determined that treatment has been effective with various physically painful ailment areas such as those listed in Table 1 within time frames of up to approximately 2 minutes which is substantially less than the approximately 2 to approximately 4 minutes that was needed with the prior art Tens Cam unit. Ultrasounds taken from various patients have shown that less inflammation exists about the body areas where these painful ailments occur.

Thus, the tool 1 shows anti-inflammatory results in the areas listed in Table 1.

TABLE 1

| AILMENTS (column 1 list) | AILMENTS (column 2 list) |
|---|---|
| Ankle Sprain | Headache |
| Tennis Elbow | Earache |
| Torn Meniscus | Sinusitus |
| Back Pain | Burns |
| Nerve Root | Wounds |
| Bursitis | Abrasions |
| Neck Pain | GERD |
| Macular Degeneration | TMJ |

TABLE 1-continued

| AILMENTS (column 1 list) | AILMENTS (column 2 list) |
|---|---|
| Hernia | Morton's Neuroma |
| Gallbladder | Arthritis |
| Foot Pain | Sore Throat |
| Scars | Shingles |

Although one of the embodiments is described using a battery and another embodiment uses a wall plug power source, either or both embodiments can use battery and wall plug power supplies as will be further described below.

Additionally, although one embodiment has been described as using a fixed frequency output, and one embodiment using a variable emission output, either or both embodiments can generate fixed frequency outputs and/or variable frequency outputs.

The operation of the amplifier unit 30 will now be described. The operator turns on the on/off switch to amplifier unit 30, and after positioning the tool 10 to be approximately 18 inches from the area of the patient that is to be treated starts adjusting the potentiometer 200. At the same time, the tens cam unit 20 is providing power to the internal induction coil 80 about crystals 70 and excites the crystals 70 to generate the approximately 8 Hz frequency to the area of the patient being treated.

When the effected area of the patient is just starting to be treated the RED LED will stay lit. As the treatment takes place, the RED LED will turn off and the GREEN LED will turn on. When only the GREEN LED is on then the effected area has been effectively treated with the tool 10. The amplifier 30 is tuned so that the GREEN LED will turn on when the external torroidal coil sensor 50 about the device 10 senses a reading from the effected area being treated by the device receives a signal between approximately 7.5 Hz and approximately 8.5 Hz.

In operation, both LEDS can initially be lit if the reading from the patient is on the border between both red and green.

Testing of the bioscanner/biosensor unit 10 was performed under the direction of several licensed physicians. When a volunteer was selected, the bioscanner unit 10 was turned on from a position of approximately 18 inches from the bare skin. The unit 10 with sensitivity adjuster (Potentiometer 200) on the amplifier 30 was used as the tool 10 was moved over the patient's body until the RED LED became lighted, which indicated a problem area.

The laser focusing indicator of a noncontact handheld battery powered thermometer then was focused on the problem area until a temperature reading was made. Similarly, a visual Analog Scale reading from the volunteer was recorded. The bioscanner unit 10 was allowed to function until the red LED went out and the green LED glowed a steady green. At this moment, the time, the temperature, the BSU number and a VAS score was recorded. This procedure was followed with each volunteer and each effected problem area on the patients that were being treated.

The bioscanner performance evaluation was accomplished using several criteria. The first criteria was the visual analogy scale (VAS) which is considered the standard for pain evaluation research studies. FIG. 13 shows a visual analogy scale (VAS) used for the testing of the invention. Generally improvement or no change was noted in all cases. This would be expected if the bioscanner unit 10 was effective. These findings suggest the device is effective in finding the primary problem as a disturbance in the human energy field. Further, in view of the fact that a significant general decline in the scores is usually evidence of less pain which is indicative of improvement.

The second criteria is the temperature change during the treatment time. The temperature was determined by means of a MS6530 infrared non contact thermometer accuracy +−0.1 degree F. The temperature varied increasing when the problem spinal area was over the sympathetic nervous system distribution and decreasing when the involved area was over the distribution of the spinal parasympathetic nervous system as might be expected.

The third criteria is Bio Scanner Units (BSU). BSU was given an arbitrary value. This was adjusted to compensate for variations in the ambient energy environment. Generally, the evaluation was continued until the Bio Scanner Units (BSU) had stabilized and the green LED remained on and constant.

The result of reviewing the procedure with due consideration of the evaluation criteria above demonstrates that the bio scanner unit 10 is functioning in a reasonable manner and performed the desired functions. Table 2 references the bio scanner unit research findings.

TABLE 2

| PERSON AREA | TIME START | TEMP START | VAS START | BSU START | TIME END | TEMP END | VAS END | BSU END |
|---|---|---|---|---|---|---|---|---|
| BM L3-S1 | 3:12 P | 93.7 F. | 6 | 455 | 3:30 P | 95.5 F. | 2 | 001 |
| GK FOOT FX | 3:338 P | 91.0 F. | 8 | 001 | 3.54 P | 92.4 F. | 4 | 453 |
| JH C4-7 | 10:16 A | 85.2 F. | 2 | 002 | 10:30 A | 83.6 F. | 2 | 455 |
| EP L2-5 | 9:28 A | 92.3 F. | 8 | 458 | 9:45 A | 88.7 F. | 6 | 001 |
| CC L4-S1 | 9.26 A | 91.5 F. | 4 | +− | 9:59 A | 90.2 F. | 0 | 738 |
| JC C2-4 | 10:39 A | 89.2 F. | 6 | +− | 10:49 A | 92.3 F. | 4 | 730 |
| JB C2-4 | 11:02 A | 86.1 F. | 8 | +− | 11:15 A | 92.1 F. | 6 | 712 |

The symbols and terms in TABLE 2 are defined below:
TEMP. START-Temperature of Inflamed Area Before Treatment
TEMP. END-Temperature of Inflamed Area After Treatment
VAS START-Visual Analogy Before Treatment
  (show patient pictures shown in FIG. 13 and ask which fits their pain level)
VAST END-Visual Analogy After Treatment
  (show patient pictures shown in FIG. 13 and ask which fits their pain level)
BSU-Arbitrary (Variable Temperature-moved to steady state more blood flow)
  (warmer better circulation to surface.)
The PERSON AREAS of the treated patients are defined below.
BM L3-S1—Lower Back Pain $3^{rd}$ Lumbar $1^{st}$ Sacral Segment
GK Foot Fx—Foot Fracture and Pain
JH C4-7—Midneck Pain ($4^{th}$-$7^{th}$ Cervical Bone)
EP-L2-5—Lower Back Pain Lumbar 2-5
CC L4 S1—Back Pain $1^{st}$-$4^{th}$ Lumbar $1^{st}$ Sacral Segment
JC-C2-4—Neck Pain-$2^{nd}$-$4^{th}$ Cervical Vertebrae
JB-C2-4—Neck Pain $2^{nd}$-$4^{th}$ Cervical Vertebrae Table 2 is relevant since it demonstrates by numerical values the functional results of the invention results on actual patients receiving treatments. Tests have shown that the swelling will be seen to resolve first followed by normalizing of the normal tissue structure. Subjectively, pain has been shown to greatly become decreased. Objectively, testing has shown that an immediate decrease in swelling and redness will be noted. If an area of skeletal misalignment, was being treated the misalignment is usually corrected along with the pain, swelling and stiffness.

FIG. 10 shows the printed circuit board. FIGS. 11A and 11B show a schematic of the printed circuit board. Referring to FIGS. 10, 11A and 11B, INPUT A and INPUT B, is a differential-input high gain Amplifier TC084 (OP AMP) circuit. It has a gain at 500 with the 3 inverting amplifier stages. Then, IC2, the 741 (Op Amp) acts as a comparator, with respect to the "Ambient Level" Adjustment, R9. The rest is what is used to illuminate (opposite states) Red or Green LEDs. The opto-isolator provides an isolated "clear-cut" switching function, which is followed by the respective INVERTER/Buffers (4049) to illuminate, alternatively either RED or GREEN LEDs. If RED is illuminated (is on), then GREEN is off. If GREEN is illuminated (is on), then RED is off.

PINS 1, 2 and 3 comprise the first Amplification Stage (Op Amp). The gain of the Amplifier is determined by the ratio of resistor values. The second stage of the Amplifier is that of (Op Amp) with PINS 5, 6 and 7. Gain can be set by resistor values. The third and final, amplification stage is comprised of (Op Amp) with PINS 8, 9 and 10. It only has a gain (Av) of 5, whereas, the first 2 stages have a gain (Av) of 10 each. Therefore, the total gain of the Amplification stages (1×2×3)=Av=10(first stage)×(times) Av=10 (second stage) equals=100 (Av 1 of first 2 stages combined then×5 equals (Av) gain (over all) with all 3 stages of 500. Therefore, the circuit of FIGS. 10, 11A and 11B is a very sensitive, high gain amplifier circuit.

The Opto-isolator provides isolation from the power supply used for the operational amplifiers and comparators, yet is effectively switched by the output of the comparator, IC2 (either "on" or "off"). This acts as the input to the inverter, which operates the LEDs, alternately, depending on level sensed and compared to "ambient."+5 volts was measured at "Node V+". 0.3 volts maximum "Registered" as Logic "0". The voltage "swing" at PIN 2 of IC 2 was less than 5 volts under all test conditions. Green LED would not turn off unless "pull down resistor (R12)" is employed.

Figure 12A:
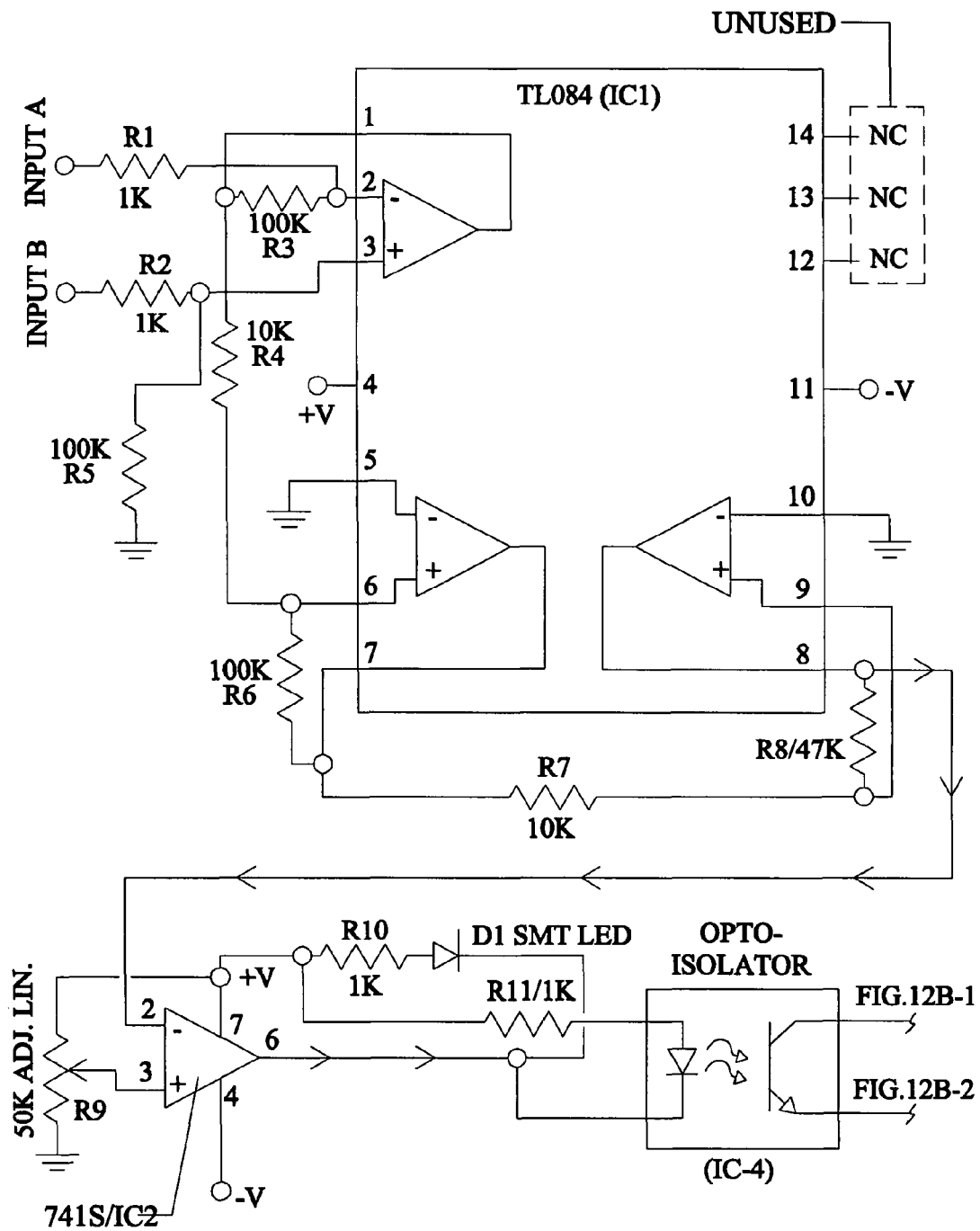
FIG. 12A is another schematic of the printed circuit board similar to FIGS. 11A-11B.
Figure 12B:
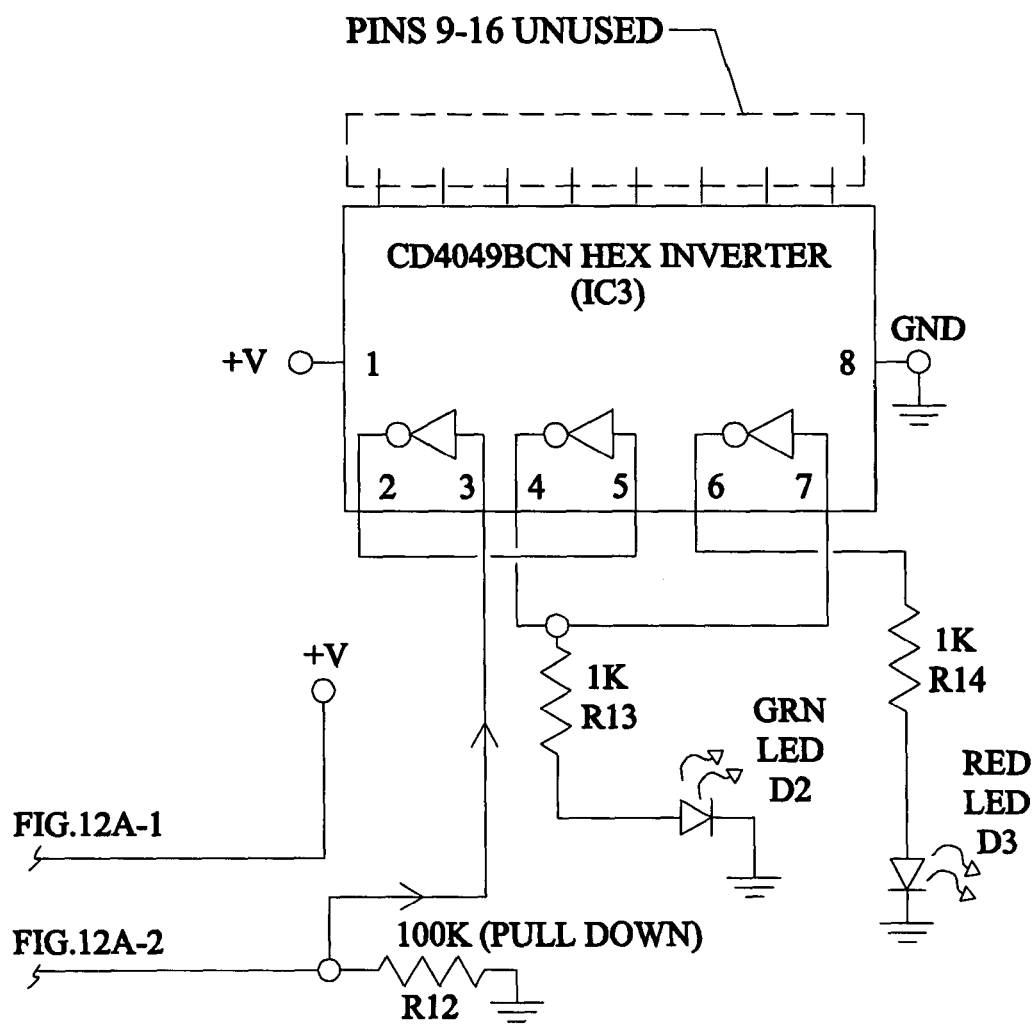
FIG. 12B is a continuation of the schematic shown in FIG. 12A.

FIGS. 12A and 12B shows another schematic of the printed circuit board that is equivalent to the circuit shown in FIGS. 11A and 11B.

The crystals modulate the local scalar field in a manner that corrects the ailments being treated, which can be inferred from the fact that there is minimal electromagnetic energy involved. The magnetic fields being generated by the two currents in the bi-filar winding are opposite and very close to being equal, which cause a very low composite magnetic field. The voltages involved in the power source are also low and not likely to be a factor in the treatment process.

When two electrons collide, a photon is generated. When two electrons pass in a near miss condition, a virtual photon is generated. Virtual electrons have all the characteristics that photons do, except that they are not visible. The bi-filar winding around the crystal is designed to generate as many electron near misses as possible by passing currents the two conductors in the by-filar wire in opposite directions. The virtual photons generated in the close proximity to the crystal, cause crystal to do whatever it does to modulate the local scalar field in a way that corrects the ailments being treated. The crystal does not resonate at 8 Hertz, but it is energized by the virtual photons being generated by the currents which are generated by a power source that is being switched on and off at a rate of approximately 8 Hertz.

The novel invention can be powered by a wall plug, batteries, combinations thereof, and the like. The novel flashlight shaped version of the invention can be powered by a manual windup generator in an ergonomically shaped casing as shown in the other parent patent application Ser. No. 11/441,483 filed May 26, 2006, now U.S. Pat. No. 7,883,534, which is also incorporated by reference.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method of treating patients with a handheld device, comprising the steps of:
    providing a portable housing;
    mounting an induction coil wrapped about at least one crystal inside the housing;
    providing a torroidal coil wrapped about a ferrous coil form, that is connected to an amplifier as a sensor-receiver
    mounting the sensor-receiver with the portable housing;
    mounting at least one light source adjacent to the portable housing;
    powering the induction coil to excite the at least one crystal from a power source;
    generating an emission from the housing, wherein the emission is adapted to be used for treatment of an area of a patient, and the housing is adapted to be held by an operator;
    sensing energy from the area with the sensor-receiver; and
    illuminating the at least one light source when the sensed energy is adapted to indicate the area is being treated.

2. The method of claim 1, wherein the at least one light source includes: a first colored light emitting diode (LED) and a second colored light emitting diode(LED).

3. The method of claim 2, further comprising the steps of:
    illuminating the first LED when the sensed energy is less than approximately 7.5 or is greater than approximately 8.5 Hz,; and
    illuminating the second LED to indicate when the sensed energy has a wavelength in the range of approximately 7.5 to approximately 8.5 Hz.

4. The method of claim 3, further comprising the steps of:
    providing a red colored LED as the first LED; and
    providing a green colored LED as the second LED.

5. The method of claim 1, wherein the at least one crystal includes: dimensions of approximately 1 inch long by approximately ¼ inch in diameter.

6. The method of claim 1, further comprising the step of:
    providing a lens in front of the at least one crystal for focusing and diffusing the generated emission.

7. The method of claim 6, further comprising the step of:
    providing a sphere as the lens in front of the at least one crystal.

8. The method of claim 1, further comprising the step of:
    providing three elongated crystals as the at least one crystal, the three elongated crystals being arranged in a triangular configuration with one another inside of the housing.

9. The method of claim 8, wherein the illuminating step includes the step of:
    illuminating the at least one light source when the area emits energy within the range of approximately 7.5 to approximately 8.5 Hz.

10. The method of claim 8, further comprising the step of:
    providing Lemurian crystals for the three elongated crystals.

11. The method of claim 10, further comprising the step of:
    providing each of the three elongated crystals with dimensions of approximately 1 inch long by approximately ¼ inch in diameter.

12. The method of claim 1, further comprising the step of:
    providing a bifilar coil wrap about the crystals so that the at least one crystal is wrapped in a bundle.

13. A portable treatment device, comprising:
    a portable housing adapted to be held by a treatment operator;
    an induction coil wrapped about at least one crystal inside the housing;
    a first colored light source and a second colored light source with the portable housing, the second light source being a different color from the first light source;
    a power source connected to the induction coil to excite the at least one crystal, wherein the treatment device emits an emission adapted to be used for treatment of an area of a patient, and
    a sensor-receiver comprising a torroidal coil wrapped about the housing, the torroidal coil connected to an amplifier, the sensor-receiver adapted for sensing energy from the area of the treatment, and the sensor-receiver for illuminating one of the first and the second colored light sources when the sensed energy is below or above a selected wavelength range, and for illuminating another one of the first and the second colored light sources when the sensed energy is in the selected wavelength range.

14. The portable treatment device of claim 13, wherein each of the first light source and the second light source includes a light emitting diode (LED).

15. The portable treatment device of claim 14, wherein the first light source is illuminated when the sensed energy is less than 7.5 or is greater than 8.5 Hz, and the second light source is illuminated when the sensed energy has a wavelength in the range of 7.5 to 8.5 Hz.

16. The portable treatment device of claim 15, further comprising:
    a red colored LED as the first light source; and
    a green colored LED as the second light source.

17. A handheld treatment device, comprising:
    a portable housing;
    an induction coil wrapped about at least one crystal inside the housing;
    a sensor-receiver comprising a torroidal coil wrapped in a coil form mounted to the housing, the torroidal coil being connected to an amplifier;
    at least one light source adjacent to the portable housing; and a power source for powering the induction coil to excite the at least one crystal to generate an emission from the housing, wherein the emission is adapted to be used for treatment of an area of a patient, and the sensor-receiver is adapted for sensing energy from the area and for illuminating the at least one light source when the sensed energy is indicates the area is being treated.

\* \* \* \* \*